US00PP21332P2

(12) United States Plant Patent
Takamura

(10) Patent No.: US PP21,332 P2
(45) Date of Patent: Sep. 28, 2010

(54) ***VIOLA* PLANT NAMED 'SUNVIOPOKI'**

(50) Latin Name: *Viola cornuta*
Varietal Denomination: Sunviopoki

(75) Inventor: Naoto Takamura, Yamanashi (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/456,338

(22) Filed: Jun. 15, 2009

(51) Int. Cl.
*A01H 5/00* (2006.01)

(52) U.S. Cl. ..... Plt./323

(58) Field of Classification Search ..... Plt./323
See application file for complete search history.

*Primary Examiner*—Annette H Para

(57) ABSTRACT

A new and distinct cultivar of *Viola* plant named 'Sunviopoki', characterized by its trailing and mounding plant habit; freely branching habit; freely flowering habit; and blue and yellow bi-colored flowers.

1 Drawing Sheet

Botanical designation: *Viola cornuta.*
Cultivar denomination: 'SUNVIOPOKI'.

BACKGROUND OF THE INVENTION

The present invention relates to a new and distinct cultivar of *Viola* plant, botanically known as *Viola cornuta* and hereinafter referred to by the name 'Sunviopoki'.

The new *Viola* plant is a product of a planned breeding program conducted by the Inventor in Higashiomi, Shiga, Japan. The objective of the breeding program was to create new trailing and freely branching *Viola* cultivars with unique and attractive flower coloration.

The new *Viola* plant originated from a cross-pollination made by the Inventor in April, 2003, in Higashiomi, Shiga, Japan, of a proprietary selection of *Viola cornuta* identified as code number 0V-40-1, not patented, as the female, or seed, parent with a proprietary selection of *Viola cornuta* identified as code number 02VC22, not patented, as the male, or pollen, parent. The new *Viola* was discovered and selected by the Inventor as a single flowering plant within the progeny of the stated cross-pollination in a controlled greenhouse environment in Higashiomi, Shiga, Japan in April, 2004.

Asexual reproduction of the new *Viola* plant by vegetative cuttings in a controlled greenhouse environment in Higashiomi, Shiga, Japan since May, 2004, has shown that the unique features of this new *Viola* plant are stable and reproduced true to type in successive generations.

SUMMARY OF THE INVENTION

Plants of the new *Viola* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunviopoki'. These characteristics in combination distinguish 'Sunviopoki' as a new and distinct cultivar of *Viola:*

1. Trailing and mounding plant habit.
2. Freely branching habit.
3. Freely flowering habit.
4. Blue and yellow bi-colored flowers.

Compared to plants of the female parent selection, plants of the new *Viola* differ primarily in flower color as plants of the female parent selection have yellow-colored flowers. In addition, plants of the new *Viola* have smaller flowers than plants of the female parent selection.

Compared to plants of the male parent selection, plants of the new *Viola* differ primarily in flower color as plants of the male parent selection have darker blue and yellow bi-colored flowers. In addition, plants of the new *Viola* have larger flowers than plants of the male parent selection.

Plants of the new *Viola* can also be compared to plants of the *Viola cornuta* 'Sunviobuho', disclosed in U.S. Plant Pat. No. 16,557. In side-by-side comparisons conducted in Higashiomi, Shiga, Japan, plants of the new *Viola* and 'Sunviobuho' differed in the following characteristics:

1. Plants of the new *Viola* were more freely branching than plants of 'Sunviobuho'.
2. Plants of the new *Viola* had larger flowers than plants of 'Sunviobuho'.
3. Plants of the new *Viola* and 'Sunviobuho' differed in flower color.

BRIEF DESCRIPTION OF THE PHOTOGRAPHS

The accompanying colored photographs illustrate the overall appearance of the new *Viola* plant, showing the colors as true as it is reasonably possible to obtain in colored reproductions of this type. Colors in the photographs may differ slightly from the color values cited in the detailed botanical description which accurately describe the colors of the new *Viola* plant.

The photograph at the top of the sheet comprises a top perspective view of a typical flowering plant of 'Sunviopoki' grown in a container.

The photograph at the bottom of the sheet is a close-up view of typical flowers of 'Sunviopoki'.

DETAILED BOTANICAL DESCRIPTION

The aforementioned photographs and following observations, measurements and values describe plants grown in Higashiomi, Shiga, Japan, under commercial practice during the autumn and winter in a polyethylene-covered greenhouse with day temperatures averaging 10° C. and night temperatures averaging 5° C. Plants were five and eight months old when the description and photographs, respectively, were taken. In the following description, color references are made to The Royal Horticultural Society Colour Chart, 2001 Edition, except where general terms of ordinary dictionary significance are used.

Botanical classification: *Viola cornuta* 'Sunviopoki'.

Parentage:

*Female, or seed, parent.*—Proprietary selection of *Viola cornuta* identified as code number 0V-40-1, not patented.

*Male, or pollen, parent.*—Proprietary selection of *Viola cornuta* identified as code number 02VC22, not patented.

Propagation:

*Type.*—By vegetative cuttings.

*Time to initiate roots, summer.*—About two weeks at 20° C. to 25° C.

*Time to initiate roots, winter.*—About two weeks at 15° C. to 20° C.

*Time to produce a rooted young plant roots, summer.*—About four weeks at 20° C. to 25° C.

*Time to produce a rooted young plant roots, winter.*—About four weeks at 15° C. to 20° C.

*Root description.*—Fine, fibrous; white in color.

*Rooting habit.*—Freely branching.

Plant description:

*Plant form/habit.*—Trailing and mounding plant habit; vigorous growth habit; freely branching habit, pinching enhances branching.

*Plant height.*—About 11.2 cm.

*Plant width* (*spread*).—About 38.6 cm.

*Lateral branches.*—Length: About 12.6 cm. Diameter: About 1.9 mm. Internode length: About 1.2 cm. Strength: Strong. Texture: Smooth, glabrous. Color: Close to 144B.

Foliage description:

*Arrangement.*—Alternate, simple.

*Length.*—About 3 cm.

*Width.*—About 1.6 cm.

*Shape.*—Ovate.

*Apex.*—Obtuse.

*Base.*—Cuneate.

*Margin.*—Crenate.

*Texture, upper and lower surfaces.*—Smooth, glabrous.

*Venation pattern.*—Pinnate; reticulate.

*Color.*—Developing and fully expanded leaves, upper surface: Close to 146B; venation, close to N144C. Developing and fully expanded leaves, lower surface: Close to 138B; venation, close to N144D.

*Petiole.*—Length: About 2.9 cm. Diameter: About 0.8 mm. Texture, upper and lower surfaces: Smooth, glabrous. Color, upper and lower surfaces: Close to 144B.

*Stipule.*—Length: About 2.1 cm. Diameter: About 1 cm. Shape: Pinnately-parted. Apex: Acute. Base: Cuneate. Texture, upper and lower surfaces: Smooth, glabrous. Color, upper surface: Close to 146B. Color, lower surface: Close to 138B.

Flower description:

*Flower type/habit.*—Single flowers borne in upper leaf axils; flowers face outwardly; freely flowering habit with about 45 flowers per plant.

*Fragrance.*—Slightly scented; pleasant.

*Natural flowering season.*—Plants begin flowering about eight to ten weeks after planting; continuously flowering from early November to May in Japan.

*Postproduction longevity.*—Flowers last about five to seven days on the plant; flowers not persistent.

*Flower buds.*—Height: About 1.9 cm. Diameter: About 5 mm. Shape: Lenticular. Color: Close to 96C.

*Flower diameter.*—About 4.3 cm by 3.6 cm.

*Flower depth.*—About 1.5 cm.

*Eye diameter.*—About 2.8 mm by 4.1 mm.

*Petals.*—Quantity per flower: Five in a single whorl; two upper petals, two lateral petals and one lower petal, spurred. Upper petals: Length: About 2.4 cm. Diameter: About 2.1 cm. Shape: Obovate with rounded to truncate apex and attenuate base; margin, entire and slightly undulate. Texture, upper and lower surfaces: Smooth, glabrous. Color: Developing and fully expanded petals, upper surface: Close to 94C. Developing and fully expanded petals, lower surface: Close to 93D. Lateral petals: Length: About 1.9 cm. Diameter: About 1.6 cm. Shape: Rounded to elliptic with rounded apex and attenuate base; margin, entire and slightly undulate. Texture, upper and lower surfaces: Smooth, glabrous. Color: Developing and fully expanded petals, upper surface: Initially close to 154D and becoming closer to 94D; at the margins, close to 94D; stripes at base, close to N89A; at the base, close to 6A. Developing and fully expanded petals, lower surface: Close to 94D; center, close to 154D. Lower petal: Length: About 1.9 cm. Diameter: About 2.5 cm. Shape: Reniform with emarginate apex and attenuate base; margin, entire and slightly undulate. Texture, upper and lower surfaces: Smooth, glabrous. Color: Developing and fully expanded petals, upper surface: Close to 6A; toward the margins, between 92C and 94D; stripes, close to N92A. Developing and fully expanded petals, lower surface: Close to 4B; towards the margins, close to 97B. Eye color: Close to 13A. Spur length: About 6.3 mm. Spur diameter: About 1.1 mm. Spur color: Close to 189B.

*Sepals.*—Quantity per flower: Typically five in a single whorl. Length: About 1.7 cm. Width: About 4 mm. Shape: Lanceolate. Apex: Acute. Base: Truncate. Margin: Entire. Texture, upper and lower surfaces: Smooth, glabrous. Color, upper and lower surfaces: Close to 138B.

*Peduncles.*—Length: About 9.1 cm. Diameter: About 1.2 mm. Texture: Smooth, glabrous. Color: Close to 144A.

*Reproductive organs.*—Stamens: Quantity per flower: Typically five. Anther shape: Ellipsoidal. Anther size: About 3.7 mm by 1.5 mm. Anther color: Close to 155A; towards the apex, close to 175C. Pollen amount: Scarce. Pollen color: Close to 10D. Pistils: Quantity per flower: One. Pistil length: About 5.8 mm. Stigma shape: Ellipsoidal. Stigma color: Close to 151D. Style color: Close to 154D. Ovary color: Close to 144C.

*Seed/fruit.*—Seed and fruit development have not been observed.

Disease/pest resistance: Plants of the new *Viola* have not been noted to be resistant to pathogens and pests common to *Viola*.

Garden performance: Plants of the new *Viola* have been observed to have good garden performance and to tolerate rain, wind and temperatures from about −7° C. to about 25° C.

It is claimed:

1. A new and distinct *Viola* plant named 'Sunviopoki' as illustrated and described.

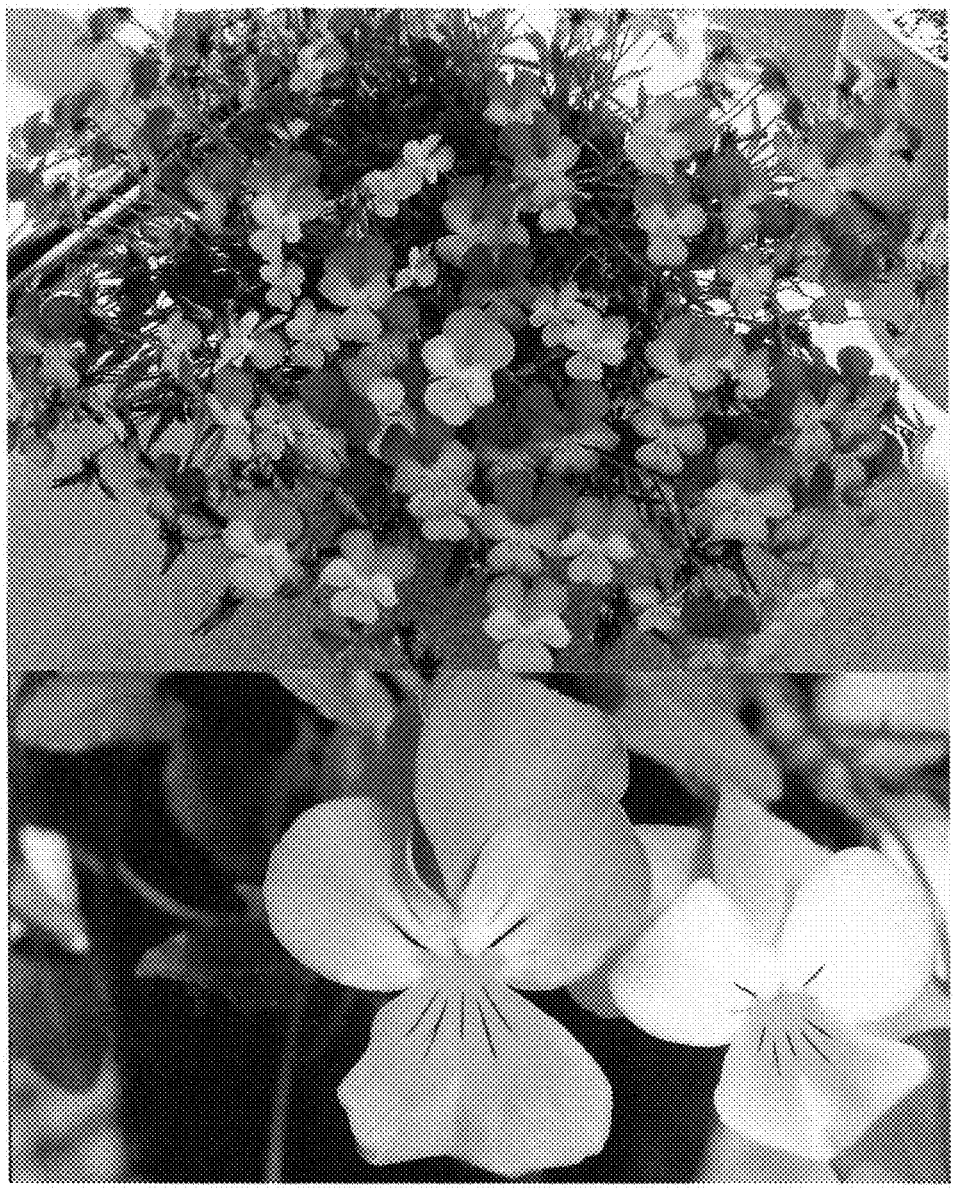

* * * * *